US00PP18655P2

(12) United States Plant Patent
Pieters

(10) Patent No.: US PP18,655 P2
(45) Date of Patent: Mar. 25, 2008

(54) *CHRYSANTHEMUM* PLANT NAMED 'PPP CON Y05'

(50) Latin Name: *Chrysanthemum morifolium*
Varietal Denomination: PPP CON Y05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 53 days.

(21) Appl. No.: 11/414,886

(22) Filed: Apr. 29, 2006

(51) Int. Cl.
*A01H 5/00* (2006.01)

(52) U.S. Cl. ..... Plt./289
(58) Field of Classification Search ..... Plt./289
See application file for complete search history.

(56) References Cited

U.S. PATENT DOCUMENTS

PP9,818 P * 3/1997 VandenBerg ..... Plt./289
PP11,903 P2 * 6/2001 Glicenstein ..... Plt./289

OTHER PUBLICATIONS

Broertjes et al. Applications of Mutation Breeding Methods in the Improvement of Vegetatively Propagated Crops, 1978, pp. 162–175.*

Winter. Southern Gardening Early–season mums add landscape sizzle. Mississippi State University Office of Agricultural Communications 2005, [online], retrieved on Aug. 15, 2007. Retreived from the Internet <http://msucares.com/news/print/sgnews/sg05/sg050922.html> 2 pages.*

* cited by examiner

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, bright yellow ray florets, free branching habit, and a consistent natural season flowering habit during the second week of September.

1 Drawing Sheet

Latin name of the genus and species: *Chrysanthemum morifolium.*
Variety denomination: 'PPP CON Y05'.

BACKGROUND OF THE INVENTION

The new cultivar 'PPP CON Y05' is a product of an induced mutation of the parent *Chrysanthemum* plant variety 'PPP CON OR05' (U.S. Plant Pat. No. 18,094) using gamma ray treatment at a dose of 20 Gy. The new cultivar was discovered and selected by Dirk Pieters in September 2003 in Oostnieuwkerke, Belgium.

Asexual reproduction of the new cultivar 'PPP CON Y05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP CON Y05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP CON Y05.' These characteristics in combination distinguish 'PPP CON Y05' as a new and distinct *Chrysanthemum* cultivar:

1. Large bright yellow inflorescences;
2. Consistent flowering response to short days, blooming consistently after 49 days of short day length;
3. Free branching habit; and
4. Consistent natural season flowering habit during the second week of September.

Plants of the new cultivar 'PPP CON Y05' are similar to plants to the parent variety, 'PPP CON OR05,' in most horticultural characteristics, however plants of the new cultivar 'PPP CON Y05' are smaller in height than the parent. Also, 'PPP CON Y05' have a larger inflorescence diameter. Finally, the ray florets of 'PPP CON Y05' are bright yellow compared to the orange ray florets of the parent.

In comparison to the commercially available variety 'GEDI ONE AVI' (U.S. Plant Pat. No. 13,455), 'PPP CON Y05' has a much wider plant spread. Additionally, the new variety 'PPP CON Y05' has lighter, greener foliage. Further, the new variety 'PPP CON Y05' has a longer inflorescence longevity and the ray florets are a much brighter, truer yellow than the yellow-orange ray florets of the comparable variety 'GEDI ONE AVI.'

BRIEF DESCRIPTION OF THE PHOTOGRAPH

The accompanying photograph in FIG. 1 illustrates in full color a typical plant of 'PPP CON Y05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP CON Y05' plants grown in Oxnard, Ventura County, Calif., during the months of the May through September. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP CON Y05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 25 cm.
Plant spread: Approximately 50 cm.
Growth rate: Moderate.
Branching characteristics: Free Branching.
Length of lateral branches: Approximately 21 cm.
Number of leaves per lateral branch: Approximately 30.
Age of plant described: Approximately 125 days.

FOLIAGE

Leaf:
- *Arrangement.*—Alternate single.
- *Average length.*—Approximately 4.3 cm.
- *Average width.*—Approximately 3.5 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1.5 cm.
- *Color.*—Young foliage upper side: Near Green 137A. Young foliage under side: Near Green 137C. Mature foliage upper side: Near Green 137A. Mature foliage under side: Near Green 137B.
- *Venation.*—Type: Palmately net. Venation color upper side: Near Green 138C. Venation color under side: Near Green 138C.

Petiole:
- *Average length.*—Approximately 1.4 cm.
- *Color.*—Near Green 138A.
- *Diameter.*—Approximately 0.01 cm.
- *Petiole texture.*—Lightly pubescent.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately second week in September.
- *Number of inflorescences per lateral branch.*—Approximately 19.
- *Inflorescence diameter.*—Approximately 6 cm.
- *Inflorescence depth.*—Approximately 1 cm.
- *Inflorescence longevity on plant.*—Approximately 28 to 32 days.
- *Persistence.*—Persistent.

Ray florets:
- *Appearance.*—Matte.
- *Texture.*—Smooth on both the upper and lower surfaces.
- *Average number of ray florets per inflorescence.*—240.
- *Shape.*—Oblanceolate.
- *Aspect.*—Flat.
- *Margin.*—Entire.
- *Apex.*—Obtuse.
- *Length.*—Approximately 2.6 cm.
- *Width.*—Approximately 0.9 cm.
- *Color.*—Upper surface at first opening: Near Yellow 9A. Upper surface at maturity: Near Yellow 9A. Upper surface at fading: Near Yellow 9B. Under surface at first opening: Near Yellow 9B. Under surface at maturity: Near Yellow 9C. Under surface at fading: Near Yellow 9D.

Disc florets:
- *Appearance.*—Shiny.
- *Texture.*—Smooth.
- *Average number of florets per disc.*—Approximately 5.
- *Shape.*—Cylindric.
- *Apex.*—Obtuse.
- *Average length.*—Approximately 0.3 cm.
- *Average width.*—Approximately 0.1 cm.
- *Color.*—At first opening: Near Yellow 9B. At maturity: Near Yellow 9A. At fading: Near Yellow-Orange 15B.

Peduncle:
- *Length.*—At terminal end (shortest): Approximately 3.9 cm. At lateral end (longest): Approximately 7.9 cm.
- *Angle to stem.*—Acute.
- *Strength.*—Moderate.
- *Color.*—Near Green 138B.
- *Habit.*—Upright.
- *Diameter.*—Approximately 0.1 cm.
- *Surface texture.*—Lightly pubescent.

Inflorescence bud:
- *Length.*—Approximately 0.5 cm.
- *Diameter.*—Approximately 0.8 cm.
- *Form.*—Globular.
- *Color.*—Near Green 141D.

Involucral bracts (phyllaries):
- *Appearance.*—Matte.
- *Texture.*—Lightly pubescent.
- *Number.*—Approximately 25.
- *Shape.*—Ovate.
- *Margin.*—Entire.
- *Apex.*—Acute.
- *Length.*—Approximately 1 cm.
- *Width.*—Approximately 0.2 cm.
- *Color.*—Upper side: Near Green 137A. Under side: Near Green 137C.

REPRODUCTIVE ORGANS

Ray florets:

*Number of pistils per floret.*—1.
*Stigma shape.*—2 branched.
*Stigma color.*—Near Yellow 9A.
*Style color.*—Near Yellow-Green 154C.
*Style length.*—Approximately 0.3 cm.
*Stamens.*—Absent.

Disc florets:

*Number of pistils per floret.*—1.
*Stigma shape.*—Cylindric.
*Stigma color.*—Near Yellow 9A.
*Style length.*—Approximately 0.1 cm.
*Style color.*—Near Yellow 8C.
*Number of stamens per floret.*—Approximately 5.
*Anther shape.*—Tubular.
*Anther color.*—Near Yellow 9A.
*Pollen color.*—Near Yellow 9A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named ‘PP CON Y05’ as herein illustrated and described.

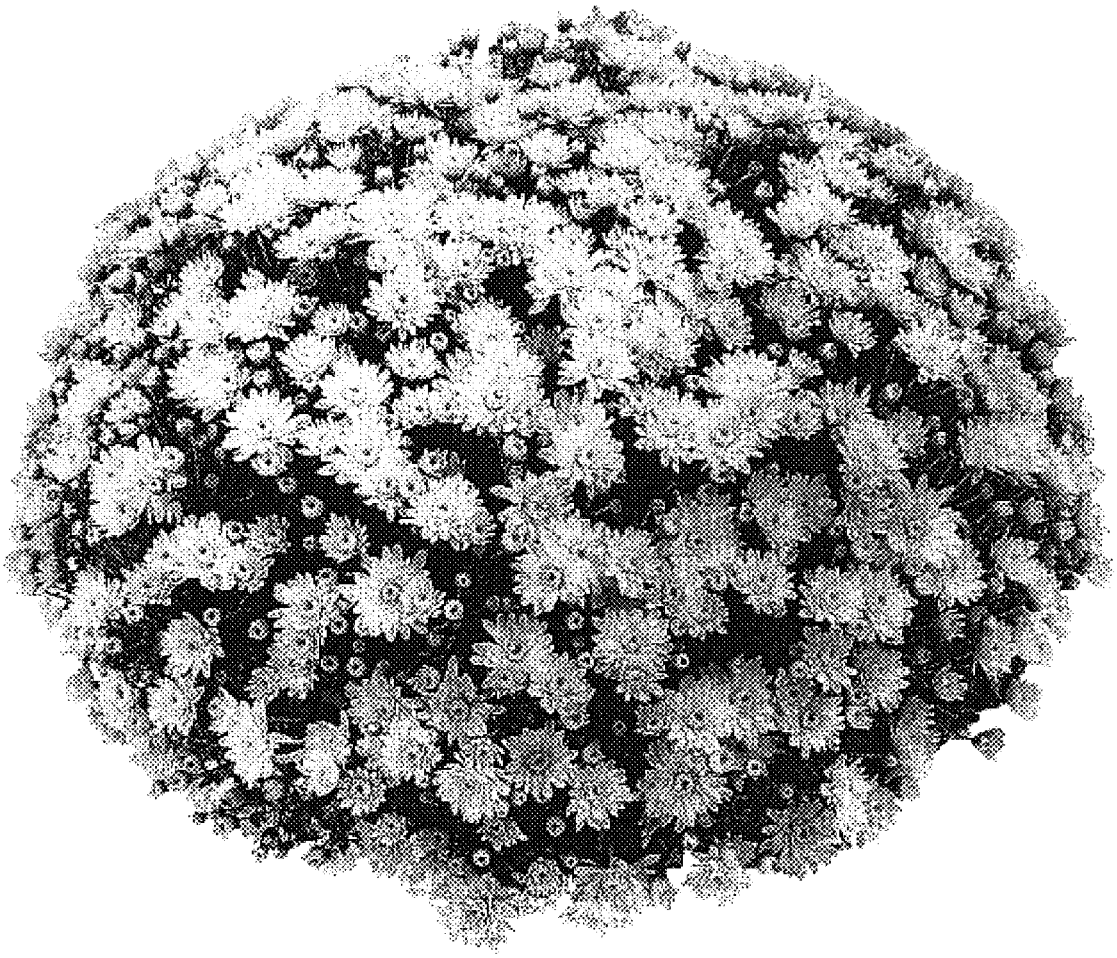

* * * * *